United States Patent
Klebba

(10) Patent No.: US 8,251,970 B2
(45) Date of Patent: Aug. 28, 2012

(54) DIAPER CLOSURE SYSTEM

(75) Inventor: Christian Klebba, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 304 days.

(21) Appl. No.: 10/438,478

(22) Filed: May 15, 2003

(65) Prior Publication Data

US 2003/0216708 A1 Nov. 20, 2003

(30) Foreign Application Priority Data

May 17, 2002 (EP) .................................... 02011033

(51) Int. Cl.
*A61F 13/15* (2006.01)
*A61F 13/20* (2006.01)

(52) U.S. Cl. ............................ 604/389; 604/391; 24/442

(58) Field of Classification Search ............. 604/385.01, 604/386–96; 24/306, 442–52

See application file for complete search history.

(56) References Cited

U.S. PATENT DOCUMENTS

| | | | |
|---|---|---|---|
| 4,615,695 A * | 10/1986 | Cooper | 604/385.15 |
| 4,662,875 A * | 5/1987 | Hirotsu et al. | 604/389 |
| 5,007,647 A * | 4/1991 | Gulick | 473/200 |
| 5,133,707 A * | 7/1992 | Rogers et al. | 604/389 |
| 5,312,387 A * | 5/1994 | Rossini et al. | 604/389 |
| 5,618,280 A * | 4/1997 | Glackin et al. | 604/385.08 |
| 5,624,429 A * | 4/1997 | Long et al. | 604/391 |
| 5,928,212 A * | 7/1999 | Kline et al. | 604/391 |
| 6,045,543 A * | 4/2000 | Pozniak et al. | 604/385.01 |
| 6,140,551 A * | 10/2000 | Niemeyer et al. | 604/367 |
| 6,375,864 B1 * | 4/2002 | Phillips et al. | 252/301.33 |
| 6,428,526 B1 * | 8/2002 | Heindel et al. | 604/391 |
| 6,572,602 B2 * | 6/2003 | Furuya et al. | 604/391 |
| 6,626,882 B2 * | 9/2003 | Hjorth | 604/392 |
| 6,740,071 B2 * | 5/2004 | Gibbs | 604/392 |
| 6,793,757 B2 * | 9/2004 | McLaughlin et al. | 156/259 |
| 6,921,570 B2 * | 7/2005 | Belau et al. | 428/103 |
| 7,276,642 B2 * | 10/2007 | Belau | 604/358 |
| 2002/0065503 A1 * | 5/2002 | Guidotti | 604/389 |
| 2002/0120245 A1 * | 8/2002 | Carlbark et al. | 604/385.01 |
| 2003/0119404 A1 * | 6/2003 | Belau et al. | 442/361 |
| 2004/0020579 A1 * | 2/2004 | Durrance et al. | 156/66 |
| 2004/0072491 A1 * | 4/2004 | Gillette et al. | 442/408 |

(Continued)

FOREIGN PATENT DOCUMENTS

EP 0 379 850 A1 8/1990

(Continued)

OTHER PUBLICATIONS

Definition of "border"—Merriam-Webster OnLine.*

(Continued)

*Primary Examiner* — Melanie Hand

(74) *Attorney, Agent, or Firm* — Charles R. Ware; Matthew P. Fitzpatrick

(57) ABSTRACT

Disclosed are diapers, and particularly baby diapers, which are made and provided to the user in a substantially flat condition. The diapers are formed into a three dimensional garment by the user and maintained in this position through use of a closure system. The closure system includes a tape type closure system with a designated zone on the diaper where the tape type closures are to be attached. Preferably the closure system includes a mechanical interlocking system known as a hook and loop fastening system or Velcro™.

15 Claims, 2 Drawing Sheets

U.S. PATENT DOCUMENTS

2004/0153046 A1 * 8/2004 Ito et al. .................. 604/391

FOREIGN PATENT DOCUMENTS

Figure 1:
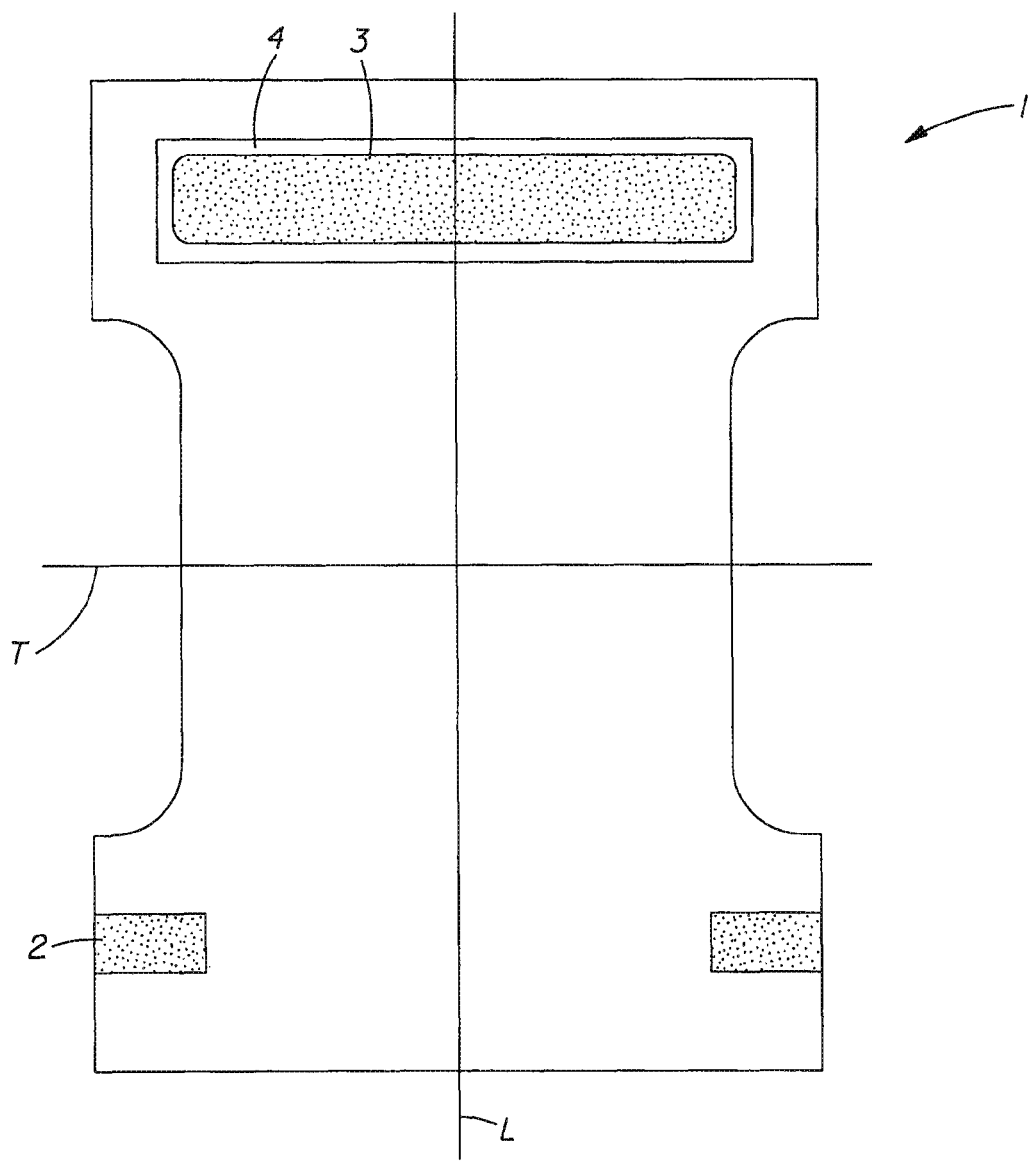

| | | | |
|---|---|---|---|
| EP | 0 756 855 A1 | | 2/1997 |
| GB | 2135568 A | * | 9/1984 |
| GB | 2 284 742 A | | 6/1995 |
| GB | 2315402 A | * | 2/1998 |
| GB | 2 296 179 A | | 6/1998 |
| JP | 59-125906 | | 8/1984 |
| JP | 1-177209 | | 12/1989 |
| JP | 6-21627 | | 3/1994 |
| JP | 10-511276 | | 11/1998 |
| JP | 2000-060899 | | 2/2000 |
| JP | 200217778 A | * | 1/2002 |
| JP | 2004-167025 | * | 6/2004 |
| WO | WO 96/19174 | | 6/1996 |
| WO | WO 01/21126 A1 | | 3/2001 |
| WO | WO 02/47597 A1 | | 6/2002 |
| WO | WO 03034966 A1 | * | 5/2003 |
| WO | WO 2005048900 A1 | * | 6/2005 |

OTHER PUBLICATIONS

Definitions of "pigment" and "darker", Merriam-Webster OnLine.*

* cited by examiner

DIAPER CLOSURE SYSTEM

FIELD OF THE INVENTION

The present invention relates to diapers, and particularly baby diapers, which are made and provided to the user of such products in a substantially flat condition. Such diapers are formed into a three dimensional garment by the diaper user and maintained in this position by means of a closure system. The closure system consists of a tape type closure system with a designated zone on the diaper where the tape type closures are to be attached. Preferably, the closure system comprises a mechanical interlocking system known as a hook and loop fastening system or Velcro™.

BACKGROUND OF THE INVENTION

Conventional diapers are made in a flat condition. The shape of such diapers is either a rectangular or hourglass. The hourglass shape is of course preferred because it provides less bulk between the legs of the baby thus facilitating a more comfortable diaper. When applying a diaper to a baby the diaper is laid out flat and the baby is sat on it approximately in the center. In this way, the rear portion can be folded up onto the baby's back and the front portion can be folded up onto the baby's belly.

Obviously this can also be done with the baby lying down. The back right and left corners of the diaper are typically attached to the front of the diaper so as to form a circular waist closure. This closure is typically facilitated by providing the back part of the diaper with attachment tapes extending from the right and left longitudinal edges. Upon closure, these tapes can be connected to a landing zone on the front of the diaper. An attachment portion of the tapes provides a releasable attachment to the landing zone.

If the closure system is adhesive, the landing zone should provide the possibility to unfasten the tapes and replace them for a better fit or for better control of the diaper. Because skin treatment aids such as cream or powders are often used in diapering, adhesive tapes have been found to be less advantageous than mechanical interlocking devices. Such mechanical devices allow closure even if contaminated with a minor quantity of cream and powder. Some mechanical interlocking systems are limited by an inability to adjust the specific location where the attachment is made. Hence the flexibility of adhesive tape closure systems and the resistance to contamination of mechanical closure systems have been combined in the so-called hook and loop fastener systems, sometimes also referred to by their trade name as Velcro™. Typically, in such closures the hook elements are provided on the tapes and the loop elements are provided in the landing zone.

These conventional systems essentially consist of a tape joined to the diaper along its longitudinal edges in the rear portion of the diaper. Such joining is usually relatively close to the rear end of the diaper. These tapes comprise hook elements capable of engaging mechanically with loops. Typically, prior to use the tapes extending outwardly from the longitudinal side edge of the diaper are folded along the longitudinal side edge of the diaper to protect the hook elements. In this condition the hook material is protected between the tape material and the inner surface of the diaper. The tapes can be held in this folded position either by adhesive means (which must be protected so as to insure that the adhesive is not exposed to the skin of the baby during use) or by mechanical engaging between the hook material itself and the inner surface of the diaper. In this latter case, the inner surface is made of a material capable of at least temporary mechanical interaction with the hooks. Many non-woven materials used for the inner surface of a diaper provide this functionality without the need for any particular manipulation. Another means of holding the tapes in this folded position is, for example, crimping.

Upon opening, the tapes have to be grabbed by the person applying the diaper to a baby. For this reason, tapes usually have a finger-tab. The finger-tab has to be optimized to provide sufficient space to be grabbed. Since not all babies like to be diapered and sometimes attempt to physically interfere with the diapering process, finger-tabs have to be easily found.

The mechanical hook fasteners have to be attached to a loop surface such that the hooks entangle with the loops and provide a sufficiently stable mechanical attachment, which resists primarily tangential forces and is not disrupted by conventional usage.

It is also important that during the closing of the diaper the landing zone is easily identifiable. This has been achieved conventionally by providing the landing zone with colors to highlight this zone relative to the surrounding diaper material. Such colors can be provided to the landing zone by any conventional methods such as printing. It also has been found that it is advantageous to provide a colored region with symmetry indicators, well known as fit-guides, with respect to the longitudinal centerline of the diaper. These indicators encourage symmetrical closure of the diaper around the waist of the baby.

It also is well known to those skilled in the art that the dimensions of the hooks and the loop-landing zone must be adjusted to each other. Apparently the landing zone must be at least as large as the hook elements on the tapes. Conventional diapers show that it is advantageous to have a landing zone which is somewhat larger in the longitudinal direction than the hook dimension in the longitudinal direction. This ensures complete engagement between the two closure system portions in the longitudinal direction. The landing zone dimension in the transverse direction is selected such that it allows free placement of the hooks to adjust the diaper circumference around the baby's waist to fit comfortably. Most usually this requires a landing zone dimension in the transverse direction of about the same as the diaper width at the front end of the diaper.

In other prior art embodiments, there is a visual aide to help a user place the hook elements of the tapes on center in the longitudinal dimension of the landing zone. This is achieved by coloring the central portion in the longitudinal direction of the landing zone and by providing a boundary portion beyond the edges of the central portion in a color which blends into the surrounding diaper material. (Typically, a white boundary can be used on a white diaper backsheet. Even more conveniently, a transparent boundary can naturally provide the same color as the backsheet). In this way, the diapering person tries to place the mechanical tape into the colored central portion. However, the person is not penalized by reduced closure performance if the placement in the central portion is not exactly met. Also known are fit guides in the landing zone to indicate a transverse distance from the tape placement to the longitudinal centerline. These guides ensure symmetrical closure of the diaper on the right and left side. For such transverse fit guides, a centrally colored landing zone with a boundary zone can be considered a centralizing closure aide in the longitudinal direction.

For even better diaper fit and comfort, tapes for diapers have been provided with elasticity. Economically, such tapes are significantly less attractive due to exorbitant material costs and consumption. Such elastic tapes have drawbacks, such as pivoting or rotating around the elastically extensible portion of the tape. Of course the same issue becomes apparent for non-elastic tapes if their longitudinal dimension is too small, i.e. if their size approaches a narrow band. In order to address this issue on non-elastic tapes a so called y-bond tape attachment has been developed. For a y-bond tape attachment, the attachment portion of the tape on the diaper is sandwiched around the diaper longitudinal edge and extended for a few millimeters beyond this edge. This reinforces the extending portion of the tape to suppress the tape rotating or pivoting effect. In elasticized tapes this problem has been addressed by providing such tapes with a significantly larger longitudinal dimension (usually without a y-bond). This adds further to the structural cost disadvantage of elasticized tapes over non-elastic tapes. Of course, elastically extensible tapes have been used as they provide a permanent adjustment of the force in a circumferential path around the waist of a baby, thereby providing a beneficial fit. It is, however, also well established in the art that this adjustment can be provided in the end regions of a diaper. It is often provided by an elasticized waistband portion (as is conventional in the textile industry for undergarments).

SUMMARY OF THE INVENTION

The present invention relates to a diaper, especially a baby diaper, with an improved closure system. The closure system comprises a landing zone, which has loop engagement elements for engaging mechanical hook fasteners, which are provided on tapes. The tapes extend beyond the longitudinal side edges of the diaper in its rearward portion. The tape as such is substantially non-elastic and comprises hook material on that tape portion which extends beyond the diaper side edges during use of the diaper. The hook fasteners and the tape preferably have the same longitudinal dimension.

The landing zone is provided on the outside of the front portion of the baby diaper. The landing zone includes the loop fasteners. It has a central portion, which is optically highlighted versus a boundary portion of the landing zone. Preferably, the optical highlighting consists of coloring the central portion with an optically distinguishable color, preferably darker or ornamentally decorated, versus the boundary portion of the landing zone. In various embodiments, the tape and the boundary portion are provided with matching decorative symbols. The central portion of the landing zone has a maximum longitudinal dimension which is smaller than the longitudinal dimension of the overall landing zone thereby ensuring that the boundary portion of the landing zone has a dimension in the longitudinal direction that makes up the difference between the central portion longitudinal dimension and the landing zone longitudinal dimension.

According to the present invention, the hook fastener longitudinal dimension is from 60% to 125%, preferably from 75% to 100%, and more preferably from 80% to 90% of the maximum longitudinal dimension of the central portion of the landing zone. Simultaneously, the longitudinal dimension of the hook fastener should preferably not be larger than the longitudinal dimension of the landing zone. According to the present invention, the tapes carrying the hook fasteners have a finger-tab, which is provided with a wavy edge thereby improving the possibility of grabbing the tape edge. It has been found that, for a tape having a longitudinal dimension of less than 50 mm, at least 4 waves with a size of less than 5 mm is useful. Other useful configurations include a tape having a longitudinal dimension of at least 35 mm, a wavy edge having at least 5 waves, and a corresponding landing zone of at least 50 mm. The number of waves and their size is a matter of selection. These selections can be readily made by a small number of trials to optimize the improved grip due to the waves and to determine the most optically pleasing variant in relation to the remainder of the tape dimensions.

BRIEF DISCUSSION OF THE FIGURES

Figure 2:
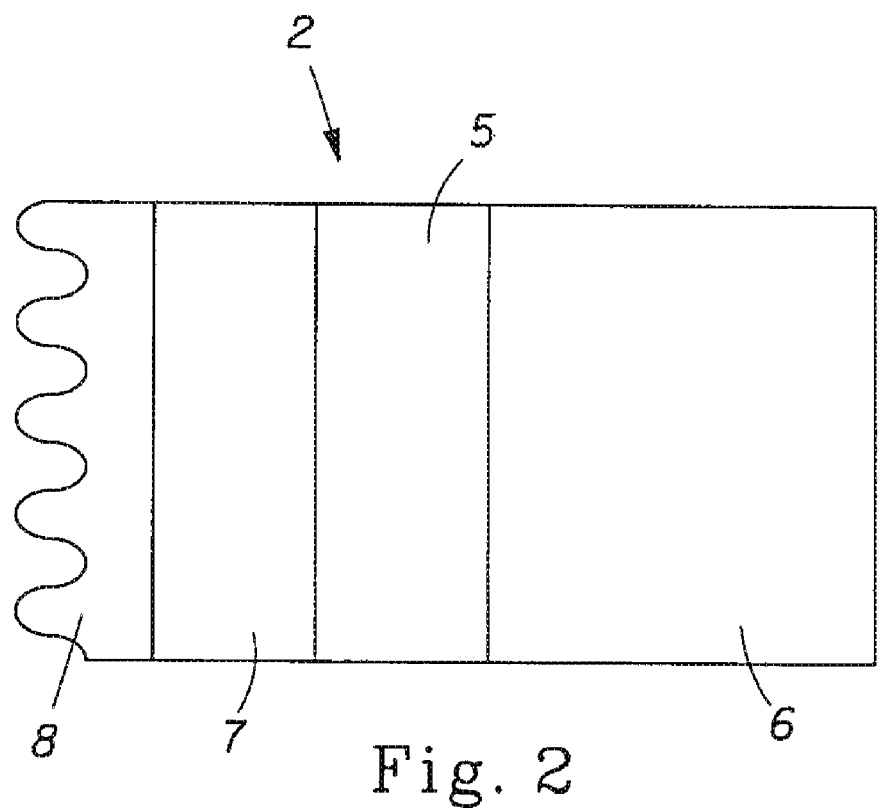

FIG. 1 shows a diaper according to the present invention.
FIG. 2 shows an enlarged schematic drawing of a closure tape according to the present invention.

DETAILED DESCRIPTION OF THE DRAWINGS

FIG. 1 shows a preferred embodiment of the diaper (1) of the present invention. In particular the dimension and sizes of the tapes, a landing zone (3,4) with a central portion (3) and a boundary portion (4) can be seen. Further, tapes (2) are shown in their tucked-in position prior to use of the diaper (1). The schematic FIG. 1 shows the diaper in a flattened-out state from the outside surface of the diaper. This side conventionally is provided with a liquid penetration retarding or liquid impervious backsheet.

In particular, FIG. 1 shows the landing zone (3,4) having the central portion (3) with its extension in a longitudinal direction that is the direction parallel to the longitudinal axis (L) as shown in FIG. 1. The central portion (3) also has a dimension in a transverse direction, which is the dimension of the central portion (3) parallel to the transverse axis (T) as shown in FIG. 1. In the embodiment shown in FIG. 1, the central portion (3) is completely surrounded by the boundary portion (4) of the landing zone. Optionally, the boundary portion need not extend completely around the central portion of the landing zone but could extend only between the central portion (3) and the end edge parallel to the transverse centerline (T) of the diaper (1). It could also be only on the respective other side of the central portion (3). The central portion need not be rectangular but can be shaped in any form useful for the purpose of aiding in longitudinal tape placement such as oval, round, rectangular-rounded. In particular, wavy outlines have been found acceptable and useful for communicating the placement aid functionality to the diapering person.

It is important to recognize that the distinction between the central portion (3) and the boundary portion (4) is not in the ability to attach to mechanical hook fasteners. The whole landing zone (3,4) comprises loop fastening elements capable of attachment to the hook fastener elements of the tapes (2). The highlighting of a central zone (3) provides a longitudinal directional fit aiding function when closing the diaper (1).

In FIG. 2 the tape (2) can be seen. The tape comprises a finger tab region (8), a region in which the mechanical hook fastener elements are provided indicated by reference numeral (7) and an attachment portion (6) by which the tape is joined to the diaper (1). This attachment portion (6) typically is provided with an adhesive, which is capable of attaching to the outside surface of the diaper, as can be seen in FIG. 1. The region (5) between this adhesive portion for attachment of the tape to the diaper and the hook fasteners can also be provided with an adhesive. Such adhesive is useful for disposing of the absorbent diaper after use. However, this need not be the case with the present invention. In fact, portion (6) and region (7) can be directly adjacent, thereby eliminating region (5).

The wavy edge of the finger tab (8) provides an additional length to this finger tab when compared to the identical amount of material used for such a finger tab with a rectangular shape. Economizing the usage of material, is of course, only possible if the tape for both sides is made from a single band of tape material, which is cut into two bands along a wavy line as disclosed in EP-A-379850.

It is important, in accordance with the present invention, that the tapes are not elastically extensible, especially not in region (5) between attachment portion (6) and mechanical hook fastening region (7). The reason for elastic extensibility, as indicated in the prior art discussion above, was to allow a more consistent force around the waist of a baby when using a diaper. However, such tapes have the disadvantage that they easily pivot or rotate in the region (5) between the portion of the tape attached to the diaper (6) and the mechanical hook fastening elements of region (7) attached to the landing zone (3,4).

According to the present invention, the materials and designs used in the diaper of the present invention are not relevant to the improvement achieved with the closure system, according to the present invention. It is, however, clear to those skilled in the art that fundamentally any improvement and desirable functionality in modern disposable absorbent diapers could and should be included in the diapers according to the present invention. This will enhance the benefit achievable by use of the improvement to the closure system according to the present invention. Reference to commercially available diapers such as Pampers™ of Procter & Gamble or Huggies™ of Kimberley-Clark in their various designs available can be used to exemplify modern diaper designs useful in the context of the present invention.

While a particular embodiment of the present invention has been illustrated and described, it would be obvious to those skilled in the art that various changes and modifications can be made without departing from the scope of the invention. It is therefore intended that the appended claims define the present invention including all such changes and modifications.

What is claimed is:

1. A diaper comprising:
   a front with a front outside surface, and a back;
   at least two, substantially non-elastic attachment tapes connected to the back, wherein each attachment tape includes a mechanical hook fastener; and
   a two-dimensional landing zone element, disposed on the front outside surface, and configured to aid in longitudinal placement of the attachment tapes on the landing zone;
   a two-dimensional central portion disposed on the front outside surface;
   a two-dimensional boundary portion, disposed on the front outside surface;
   wherein the landing zone includes:
      loop engagement elements:
         configured to engage the mechanical hook fasteners; and
         covering substantially all of the landing zone;
      the central portion:
         centered on a longitudinal centerline of the diaper; and
         visually highlighted by the boundary portion by having a color that is darker than a color of the boundary portion; and
      substantially all of the boundary portion; and
   wherein the boundary portion completely surrounds the central portion such that the visual highlighting completely surrounds the central portion.

2. The diaper of claim 1, wherein each of the hook fasteners has a largest longitudinal dimension that is from 60% to 125% of a largest longitudinal dimension of the central portion.

3. The diaper of claim 1, wherein each of the attachment tapes includes a wavy outer edge with at least four waves.

4. The diaper of claim 1, wherein each of attachment tapes has an overall longitudinal dimension of less than 50 millimeters.

5. The diaper of claim 2, wherein each of the attachment tapes includes a wavy outer edge.

6. The diaper of claim 1, wherein each of the hook fasteners has a largest longitudinal dimension that is from 75% to 100% of a largest longitudinal dimension of the central portion.

7. The diaper of claim 6, wherein each of the attachment tapes includes a wavy outer edge.

8. The diaper of claim 1, wherein each of the hook fasteners has a largest longitudinal dimension that is from 80% to 90% of a largest longitudinal dimension of the central portion.

9. The diaper of claim 8, wherein each of the attachment tapes includes a wavy outer edge.

10. The diaper of claim 1, wherein each of the attachment tapes includes a wavy outer edge with a plurality of waves.

11. The diaper of claim 10, wherein each of the waves has a maximum transverse dimension of less than five millimeters.

12. The diaper of claim 1, wherein each of the attachment tapes includes a wavy outer edge with at least five waves.

13. The diaper of claim 1, wherein each of the attachment tapes has an overall longitudinal dimension greater than or equal to 35 millimeters.

14. The diaper of claim 1, wherein each of the attachment tapes has an overall longitudinal dimension of less than 50 millimeters, each of the attachment tapes includes a wavy outer edge with at least four waves, and each of the waves has a maximum transverse dimension of less than five millimeters.

15. The diaper of claim 14, wherein each of the attachment tapes has an overall longitudinal dimension greater than or equal to 35 millimeters, each of the attachment tapes includes a wavy outer edge with at least five waves, and the landing zone has an overall longitudinal dimension of at least 50 millimeters.

* * * * *